United States Patent [19]

Regen

[11] Patent Number: 5,606,038
[45] Date of Patent: Feb. 25, 1997

[54] AMPHIPHILIC POLYENE MACROLIDE ANTIBIOTIC COMPOUNDS

[75] Inventor: Steven L. Regen, Allentown, Pa.

[73] Assignee: Competitive Technologies, Inc., Westport, Conn.

[21] Appl. No.: 419,263

[22] Filed: Apr. 10, 1995

[51] Int. Cl.$^6$ .............................. A61K 31/70; C07H 17/08
[52] U.S. Cl. .............................................................. 536/6.5
[58] Field of Search ................................. 514/31; 536/6.5

[56] References Cited

U.S. PATENT DOCUMENTS 5,204,330  4/1993  Driver et al. .............................. 514/31

OTHER PUBLICATIONS

Chemical Abstracts, vol. 123 (1995) No. 25196q. Yamashita et al "Micell/Monomer Control over . . .".

Primary Examiner—Elli Peselev
Attorney, Agent, or Firm—Yahwak & Associates

[57] ABSTRACT

Described herein is a method, and the resulting compound, for the synthesis of improved amphiphilic antibiotic agents achieved by altering the chemical structure of amphiphilic polyene macrolide compounds with an oligo(ethylene glycol) conjugate in order to raise the critical micelle concentration of the compound.

14 Claims, No Drawings

AMPHIPHILIC POLYENE MACROLIDE ANTIBIOTIC COMPOUNDS

Partial funding for the making of the invention described herein was provided by the federal government. Accordingly, the United States retains certain statutory rights in the present invention under 35 USC 200 et seq.

The actinomycete *Streptomyces nodosus* is the natural source of the antifungal agent, Amphotericin B, a polyene macrolide antibiotic having the structure:

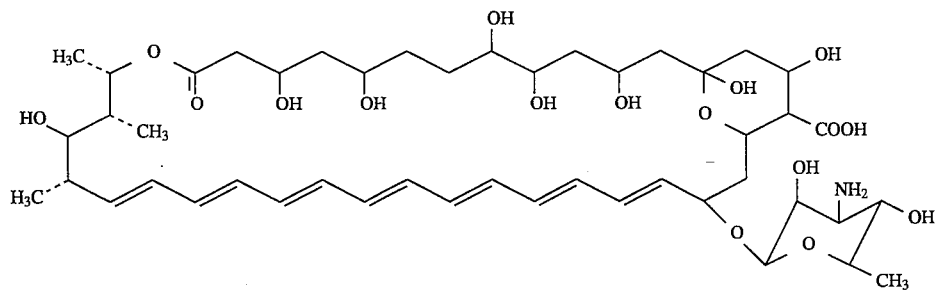

The compound contains a hydrophilic region, including a hydroxylated hydrocarbon backbone, and a sequence of seven conjugated double bonds, which is lipophilic. The compound further contains an aminodeoxyhexose, mycosamine.

*Histoplasma capsulatum, Cryptococcus neoformans*, and several species of Candida, including *C. glabrata* and *C. albicans* are sensitive to Amphotericin B ranging from 0.03 to 1.0 µg/ml in vitro. The antibiotic may be either fungistatic or fungicidal depending upon the concentration of the drug and the sensitivity of the fungus.

Amphotericin B is still, 40 years after its discovery [see U.S. Pat. No. 2,908,611], the most effective chemotherapeutic agent against most systemic mycoses.

The mechanism of action of Amphotericin B is, at least in part, dependent upon its binding to a sterol moiety, primarily ergosterol (the primary sterol found in fungal cell membranes), present in the membrane of sensitive fungi. Once this interaction occurs, the polyenes appear to form pores or channels in the fungal cell membrane which results in an increase of permeability of the membrane and the leakage of a variety of small molecules such as potassium and other ion and solute components out of the cell. This disruption in membrane integrity ultimately leads to cell death. Interactions of Amphotericin B on sterol-free membranes indicate that additional mechanisms may also be taking place.

The fact that Amphotericin B exhibits a preference to fungal membranes is the basis for its therapeutic value as a pharmaceutical. Currently, this preference is believed to be due to a stronger complexation with ergosterol than to cholesterol, the dominant sterol found in mammalian cells. However, conflicting membrane permeability data concerning Amphotericin channel ion selectivity, sterol requirements, and mode of delivery suggests that there exists a multiplicity of Amphotericin B channel structures and modes of action. Furthermore, in light of a recent finding of rupture/leakage-micelle monomer relationships, specifically that sterol-rich phospholipid membranes are prone toward "catastrophic" rupture when attacked by surfactant micelles, but are rendered leaky when "hit" by a monomeric form of the same surfactant [see J. Am. Chem. Soc. 115:708 (1993)], and the fact that Amphotericin B has a strong tendency to aggregate in solution (i.e., it has a very low critical micelle concentration) [see Biochemistry 30:5705 (1991); Biochem. Biophys. Acta, 1030:289 (1990); and Antimicrob. Agents Chemother. 36:2518 (1992)], it appeared that there might be a possibility that the intrinsic selectivity of Amphotericin B monomer might be masked by the action of micelles.

Studies have shown over the past several years that Amphotericin B and its derivatives also have potential in anti-HIV therapy, although the mechanism of this property remains obscure [see Antiviral Res. 11:119 (1989); Biochemical Pharmacol. 35:4110 (1986); and AIDS 5:1453 (1991)].

With an ever increasing number of AIDS-related fungal infections being reported, and with the potential of Amphotericin B in the treatment of HIV-infections, the therapeutic profile of Amphotericin B is of major medical importance.

The hypothesis that led to the making of the present invention was that a highly selective monomer attack by Amphotericin B, via ergosterol recognition, channel formation and resulting leakage, was hidden by a catastrophic and less discriminate attack by micelles. If correct, this would provide a rational and novel approach toward the design of improved antifungal agents acting through a mechanism of membrane disruption of the fungal cell (such agents as Amphotericin B), i.e., an approach that would design antifungal agents by raising their critical micelle concentration by way of chemical modification. The present invention provides evidence to verify this approach.

Accordingly, it is one aspect of the present invention to provide a description of an approach to design amphiphilic antibiotic agents that function by membrane disruption by altering the critical micelle concentration of the agent by chemical modification.

It is another aspect of the present invention to describe a family of unique Amphotericin B analogues that have the ability to disrupt the membrane integrity of representative fungal cells, and may thus be characterized as antifungal agents.

These and other aspects of the present invention will become more apparent to the reader with consideration of the following figures, examples and detailed description of the present invention.

More specifically, the homologous series of Amphotericin B analogues according to the present invention are ethylene glycol conjugates of the formula:

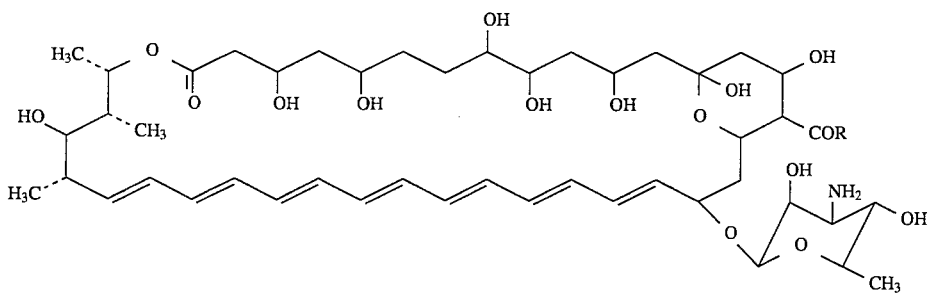

wherein R is $NH(CH_2CH_2O)_nR_1$, wherein n is an integer from 1 to 50, preferably from 1 to 20, more preferably from 1 to 17, and more preferably from 3 to 15; and wherein $R_1$ is —H, —$NH_2$, or a lower alkyl of $C_{1-6}$, preferably of $C_{1-3}$. Preferably $R_1$ is hydrogen or a lower alkyl. In one preferred conjugate of the present invention, $R_1$ is methyl. In another preferred conjugate of the present invention, n is between 3 and 15.

The experimental approach that was taken in making of the present invention was to synthesize an homologous series of Amphotericin B-oligo(ethylene glycol) conjugates of varying critical micelle concentrations, and to examine their ability to disrupt the membrane integrity of representative fungal and mammalian cells, i.e., *Candida albicans* and red blood cells (RBCs), respectively.

By the term "critical micelle concentration" of a compound is meant the concentration below which the compound exists as a non-aggregated, single molecule in solution. When the concentration of the compound exceeds its critical micelle concentration, then micelles (i.e. molecular aggregates) are formed. From preliminary studies in the making of the invention, it was found that micellar and monomer forms of the same compound can act differently on lipid membranes, i.e. micelles tend to rupture lipid bilayers, but monomer favors a much milder disruption process, one in which the membranes are made to leak intracellular components into the environment (the membranes become "leaky"). The key point of the present invention is, therefore, the discovery that by providing relatively simple poly(ethylene glycol) conjugates of amphiphilic antibiotic agents such as Amphotericin B, it is possible to significantly increase the critical micelle concentration of the agent, thus avoiding a non-selective rupture of biological membranes at high concentrations of the agent; it will be possible to maintain high selectivity of the modified agents at much higher concentrations. In short, the present invention allows for the antifungal activity of an amphiphilic agent such as Amphotericin B to be separated from its hemolytic activity by conjugation with oligo(ethylene glycol)s, and the magnitude of this separation will increase as the critical micelle concentration of the conjugate increases.

Amphotericin B conjugate of the formula:

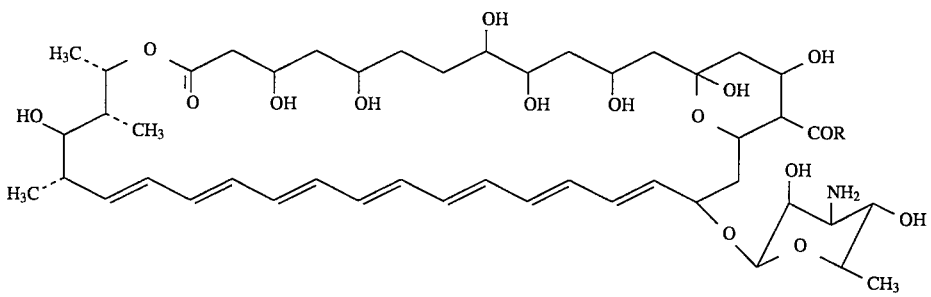

wherein R is $NH(CH_2CH_2O)_1CH_3$ was prepared according to the protocol of the following Example I:

EXAMPLE I 69.3 mg (60 μmol) of Amphotericin B was suspended in 2 ml of N,N-dimethylacetoamide (DMA), stirred at room temperature, and then stirred with 600 μmol of triethylamine, 600 μmol of diphenylphosphorylazide (DPPA), and 600 μmol of 2-methoxyethylamine (45.2 mg), in the dark and under a nitrogen atmosphere. After 115 hours, the reaction mixture was poured into 80 ml of ethyl ether. The crude product that precipitated was purified by solubilization and reprecipitation (four times) by use of $CH_3OH$/ethyl ether systems. The resulting pearl-yellow solid (72.4 mg) was further purified by silica gel chromatography (twice) using $CH_3OH$/conc. $NH_4OH$ (9/1, v/v) as the eluent to give 37.1 mg (62%) of the product. The product obtained had a low solubility (<10 μg/ml) in water, similar to that found with Amphotericin B.

Amphotericin B conjugate of the formula:

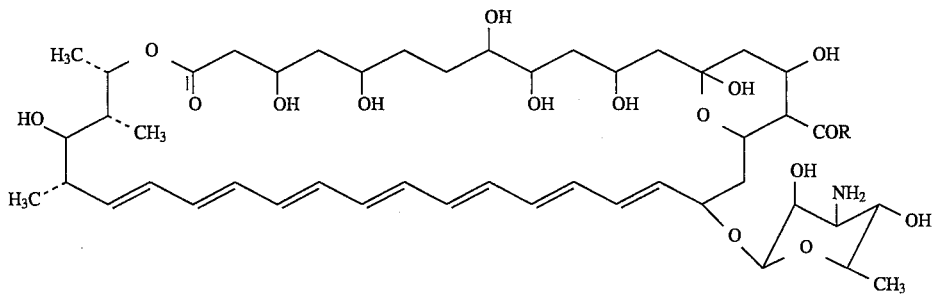

wherein R is $NH(CH_2CH_2O)_6CH_3$ was prepared according to the protocol of the following Example II:

EXAMPLE II

ω-methoxyhexaethylene glycol was initially prepared by the addition of 10 ml of a tetrahydrofuran solution containing hexaethylene glycol (4.24 g, 15 mmol) at 0° C. to a suspension of NaH (605) (0.72 g, 18 mmol) in 10 ml of dry tetrahydrofuran. Methyl iodide (1.12 ml, 18 mmol) was then added to the mixture in a drop-wise fashion. The mixture was stirred at room temperature for 5 hours, and then quenched by the addition of 0.5 ml of water. The product mixture was poured onto 70 ml of water, extracted with $CH_2Cl_2$ (6×50 ml), and the combined extracts washed with 50 ml of a saturated NaCl solution, and dried over anhydrous $Na_2SO_4$. The solvent was then removed under reduced pressure, and the residue purified by silica gel column chromatography using $CHCl_3/CH_3OH$ (9/1. v/v) as an eluent to give 1.72 g (39%) of ω-methoxyhexaethylene glycol as an oily product.

To a solution that was prepared from 5 mmol of dry hexaethyleneglycol monomethylether and 5.6 ml of triethylamine (40 mmol) in 30 ml of dry tetrahydrofuran was added 10 ml of a tetrahydrofuran solution of para-toluenesulfonyl chloride (10 mmol). This mixture was stirred for 24 hours at room temperature and then filtered. The solid precipitate was then washed with 4×10 ml of tetrahydrofuran. The combined tetrahydrofuran solutions were then concentrated under reduced pressure, and the residue was washed with 100 ml of n-hexane (three times for 30 minutes) in order to remove any excess para-toluenesulfonyl chloride. The crude product was then purified by silica gel chromatography using $CH_2Cl_2/CH_3OH$ (97/3, v/v) as eluent to give a 68% yield of ω-tosylhexaethylene glycol methylether.

ω-methoxyhexaethylene glycol (5 mmol) and 1.85 g (10 mmol) of potassium phthalimidate were mixed with 20 ml of dry N,N-dimethylformamide and stirred for 3 hours at 120° C. under a nitrogen atmosphere. The resulting mixture was then diluted with 50 ml of $CH_2Cl_2$ and a white solid that precipitated was removed by filtration and wished with 50 ml of $CH_2Cl_2$. The combined organic solutions were washed with 100 ml of 0.1N NaOH and 100 ml of saturated NaCl, and dried over anhydrous $Na_2SO_4$. Removal of solvent under reduced pressure afforded 1-phthalimidohexaethylene glycol monomer ether as an oily product, which was used directly without further purification. The crude 1-phthalimidohexaethylene glycol monomethyl ether (ca. 5 mmol) was dissolved in 30 ml of ethanol. After the solution was heated to the reflux temperature, 0.32 ml (10 mmol) of hydrazine was added. The mixture was refluxed for 1.5 hours under a nitrogen atmosphere, cooled to room temperature, and then acidified by the addition of a few drops of 6N HCl to pH 4. The resulting mixture was refluxed for an additional 1.5 hours, cooled to room temperature, ant the phthalhydrazide which precipitated was removed by filtration and washed with 2×15 ml of ethanol. The combined solvent was then evaporated at 40° C. under reduced pressure, and then 40 ml of an ethanol solution of KOH (0.55 g, 10 mmol) was added to the residue. The precipitated potassium tosylate was removed by filtration and washed with ethanol (2×15 ml). Ethanol was then evaporated, and 80 ml of $CHCl_3$ was added to the residue. The precipitated yellowish solid was removed by filtration and washed with $CHCl_3$ (2×20 ml). The combined chloroform solution was then extracted with 0.1N HCl (150 ml) and 100 ml of water. The aqueous solution was then made basic with a 1N NaOH solution (to pH 11), and extracted with methylene chloride (3×100 ml). Removal of solvent under reduced pressure, followed by purification by silica gel column chromatography utilizing $CH_3OH/NH_4OH$ (30%) (9/1, v/v) afforded a 54% yield of 1-amino-3,6,9,12,15,18-hexaoxanonadecane (i.e., ω-aminohexaethyleneglycol monomethyl ether).

Amphotericin B (115.5 mg, 0.1 mmol) and ω-aminohexaethyleneglycol monomethyl ether (1 mmol) was suspended in 2 ml of N,N-dimethylacetamide (DMA), stirred at room temperature and then treated with 1 mmol of triethylamine, 1 mmol of diphenylphosphorazidate in the dark under a nitrogen atmosphere. After 24 hours the reaction mixture was poured into 100 ml of ethyl ether. The crude product that precipitated was purified by solubilizaton-precipitation four times utilizing a $CH_2Cl_2$/ethyl ether system. The resulting pearl-yellow solid was further purified by silica gel chromatography by use of $CH_3OH/NH_4OH$ (30%) (9/1, v/v) affording a 21% recovery of the product. In contrast to Amphotericin B and the conjugate described in Example I, this conjugate gave a clear solution when dissolved in water at a concentration of 10,000 μg/ml.

Amphotericin B conjugate of the formula:

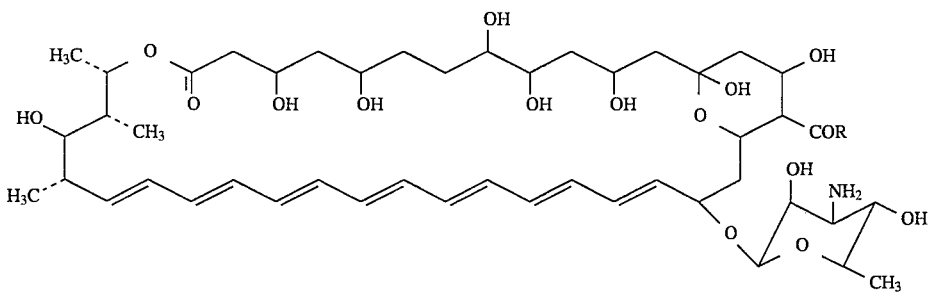

wherein R is $NH(CH_2CH_2O)_{15}CH_3$ was prepared according to the protocol of the following Example III:

EXAMPLE III

To a solution of dry polyethyleneglycol monomethyl ether (average molecular weight, 550) (5.5 g, 10 mmol) and 11.2 ml of triethylamine (80 mmol) in 40 ml of dry tetrahydrofuran was added 10 ml of a tetrahydrofuran solution of para-toluene sulfonyl chloride (3.81 g, 20 mmol). The mixture was stirred for 26 hours at room temperature, and the product mixture was then filtered and the solid washed with tetrahydrofuran (4×10 ml). Removal of solvent under reduced pressure, followed by mild heating (40° C.) and further concentration in order to remove triethylamine afforded a residue that was washed three times with 100 ml of n-hexane (30 minute washing period), in order to remove any excess para-toleunesulfonylchloride. The crude product was purified by silica gel chromatography using $CH_2Cl_2$/$CH_3OH$ (9/1, v/v) as eluent to give 5.51 g (78%) of ω-tosylpolyethylene glycol monomethylether (550) as a yellowish oil.

4.25 g (6 mmol) of ω-tosylpolyethylene glycol monomethylether and 2.22 g (12 mmol) of potassium phthalimidate was added with stirring 20 ml of dry N,N-dimethylformamide, and the resulting mixture was stirred for 3 hours at 120° C. under a nitrogen atmosphere. The yellowish resulting mixture was diluted with 50 ml of $CH_2Cl_2$ and a white solid that precipitated was removed by filtration and washed with 50 ml of $CH_2Cl_2$. The combined organic solutions were washed with 100 ml of 0.1N NaOH and 100 ml of saturated NaCl, and then died over $Na_2SO_4$. Removal of solvent under reduced pressure afforded ω-phthalimidopolyethyleneglycol monomethyl ether (550) which was used directly, without further purification. Thus, the crude ω-phthalimidopolyethyleneglycol monomethyl ether (550) (ca 6 mmol) was dissolved in 40 ml of ethanol. After the solution was warmed to the reflux temperature, 0.38 ml (12 mmol) of hydrazine was added. The mixture was refluxed for 1.5 hours under a nitrogen atmosphere, cooled to room temperature, and then acidified by the addition of a few drops of 6N HCl to pH 4. The mixture was then refluxed for 1.5 hours, cooled to room temperature, and the phthalhydrazide that precipitated was removed by filtration and washed with 2×15 ml of ethanol. The combined solvent was evaporated at 40° C. under reduced pressure, and then 40 ml of an ethanol solution of KOH (0.67 g, 12 mmol) was added to the residue. The precipitated potassium tosylate was filtered off and washed with ethanol (2×15 ml). Ethanol was then evaporated, and 80 ml of $CHCl_3$ was added to the remaining residue. The precipitated yellowish solid was filtered off and washed with $CHCl_3$ (2×20 ml). The chloroform solution was extracted with 0.1N HCl (150 ml) and 100 ml of water. The aqueous solution was then made basic with 1N NaOH solution (to pH 11), and extracted with methylene chloride (3×100 ml). Removal of solvent under reduced pressure, followed by purification by silica gel column chromatography utilizing $CH_3OH$/$NH_4OH$ (30%) (85/15, v/v) afforded a 63% yield (2.06 g) of ω-amino-polyethyleneglycol monomethyl ether (550).

Amphotericin B (115.5 mg, 0.1 mmol) and 1 mmol of ω-amino-polyethyleneglycol monomethyl ether (550) was suspended in 2 ml of N,N-dimethylacetamide, stirred at room temperature and treated with 1 mmol of triethylamine, 1 mmol of diphenyphosphorazidate in the dark under a nitrogen atmosphere. After 24 hours, the reaction mixture was poured into 100 ml of ethyl ether. The crude product that precipitated was purified four times by solubilization-precipitation using a $CH_2Cl_2$/ethyl ether system. The resulting pearl-yellow solid was further purified by silica gel chromatography by use of $CH_3OH$/$NH_4OH$ (30%) (9/1, v/v) yielding a 23% recovery. Based upon the ratio of oligoether CH2 protons (δ 3.65) to heptene protons (δ 6.03–6.42), the average chain length is estimated to be 15. In contrast to Amphotericin B and the conjugate described in Example I, this conjugate gave a clear solution when dissolved in water at a concentration of >30,000 μg/ml.

By the use of similar protocols to those described in detail in the above examples, the chain length of the repeating polyethylene subunit R in the structural formula depicted may be extended up to 50 subunits with relative ease.

In its monomeric state, Amphotericin B has a characteristic absorption band at 409 nm; upon aggregation, however, its apparent molar absorptivity decreases in magnitude [see Biochemistry 30:5707 (1991)]. Thus, by measuring its molar absorptivity as a function of the reciprocal of the macrolide concentration, one can estimate the critical micelle concentration. This can be shown mathematically by allowing T, m and P to represent the total, monomeric, and micellar concentrations (i.e. the concentration of the drug that is present in micellar form) of the macrolide, respectively, and if $\epsilon$ represents the apparent molar absorptivity and $\epsilon_m$ and $\epsilon_p$ are the molar absorptivity for the monomeric and micellar components, respectively, then it can be shown that $\epsilon = \epsilon_p + (\epsilon_m - \epsilon_p)m/T$. At concentrations in excess of the critical micelle concentration, m is a constant and $\epsilon$ is inversely proportional to T.

In order to confirm that the poly(ethylene glycol)conjugates of the present invention retain their ability to recognize ergosterol-rich bilayers, their interaction with sterol-containing large unilamellar vesicles (1000 A diameter, LUVs) by UV-vis spectroscopy using published techniques [see J. Am. Chem. Soc. 115:708 (1993)]. Incubation of a submicellar solution of the poly(ethylene glycol)conjugate of Example II (2.6 μM) with a vesicular dispersion that was 1 mM in egg PC and 0.5 mM in cholesterol, for 20 minutes at 23° C., revealed an absorption spectrum that was essentially the same as that observed in the presence of egg phosphatidyl choline vesicles (without sterol), and also the same as that found in buffer alone. In striking contrast, similar incubation with a vesicular dispersion that was 1 mM in egg phosphatidyl choline and 0.5 mM in ergosterol gave a spectrum that showed a strong diminution in the monomer band at 409 nm and new bands at 415, 390 and 375 nm; a result which is indicative of self-association and binding with ergosterol. Similar results have been obtained with Amphotericin B and with the poly(ethylene glycol) conjugates of Examples I and III. Thus, the poly(ethylene glycol) conjugates according to the present invention recognize ergosterol-rich bilayers in a way that is similar to Amphotericin B.

The concentrations of Amphotericin B and the representative Amphotericin B conjugates according to the present invention required for complete inhibition of fungal growth (MIC), and for 50% hemolysis of the human red blood cells ($K_{50}$) are provided in Table I. Specific protocols that were used for these analyses were similar to published protocols [see Biochemistry 30:5707 (1991)]. Comparison of the MIC, $K_{50}$ and cmc values for each of these compounds clearly indicate that the antifungal and hemolytic action of the macrolide becomes increasingly separated as the critical micelle of the conjugate increases.

Using the method described previously, the critical micelle concentrations for Amphotericin B and the conjugates described in the preceding examples were determined and are reported in Table I describing the aggregation, antifungal and hemolytic properties of polyethylene macrolide antibiotics (in μM amounts) according to the present invention.

TABLE I

| compound | cmc[a] | $K_{50}$[b] | MIC[c] |
|---|---|---|---|
| Amphotericin B | 1.1 | 1.8 | 1.7 |
| Example 1 | 4.4 | 7.9 | 1.6 |
| Example 2 | 25 | 42 | 2.7 |
| Example 3 | 40 | 55 | 4.3 |

[a]critical micelle concentration was determined in PBS (pH 7.4) at 37° C.;
[b]concentration required for inducing 50% release of hemoglobin from $3 \times 10^7$ cells/ml, after incubation for 1 hr at 37° C.; and
[c]minimum inhibitory concentration (see Example IV); three different strains of *Candida albicans* were tested; all tests were done in broth microdilution in yeast nitrogen base-glucose at 37° C. for 24 hours; the initial inoculum was $1 \times 10^4$ blastospores per ml The critical micelle concentration data reported in Table I indicates that elongation of the oligo(ethylene glycol) subunit within the molecule of conjugated Amphotericin B results in a continuous increase in the macrolide's critical micelle concentration. In addition, the data reported in Table I demonstrate that in order to release hemoglobin from human red blood cells, the concentration of the natural Amphotericin B as well as the concentration of each of the poly(ethylene glycol) conjugates must be greater than their critical micelle concentration; and that antifungal activity, as indicated by the MIC values, is retained below the critical micelle concentration of each conjugate. In essence, high concentrations of the Amphotericin B conjugates according to the present invention may be used as antifungal agents without disrupting red blood cells.

As can be seen in Table I, while incremental elongation of the oligo(ethylene glycol) chain led to about a 2.5-fold increase in the MIC of the macrolide (from the control Amphotericin B to the compound of Example III), the corresponding $K_{50}$ and cmc values increased by a factor of about 31 and 43, respectfully. Of special significance is the fact that all compounds in Table I show significant hemolytic activity only when their concentration exceeds their critical micelle concentration. With the exception of Amphotericin B, submicellar concentrations of each macrolide are sufficient for complete inhibition of fungal growth. That submicellar concentrations of Amphotericin B are, in fact, membrane-disrupting and cytotoxic toward *Candida albicans* was confirmed by $K^+$ release [see Biochemical Pharmacology 37:827 (1988)]. Thus, a 0.1 μM solution of Amphotericin B was sufficient for releasing 50% of the $K^+$ that was present in $3 \times 10^7$ fungal cells/ml; for similar releases by the three exemplified macrolides according to the present invention, submicellar concentrations for increasing sized macrolides of 0.8, 1.0 and 1.2 μM were required. In order to release 50% of the K+ from red blood cells, however, concentrations of Amphotericin B and the compounds of Examples I, II and III had to be essentially at their critical micelle concentrations.

The minimum inhibitory concentration reported in Table I was obtained, and further confirmed as reported in Table II, by the methods described in the following Example IV.

EXAMPLE IV

Microorganism inocula was harvested from one to five day old cultures grown on Sabourand's dextrose agar. After two washes with sterile saline, the inocula were counted utilizing a hemacytometer and diluted or concentrated as required to $1 \times 10^4$ blastospores per ml. Sterile molten agar (at 50° C.) was inoculated, allowed to cool, and 10 mm diameter discs impregnated (from 1, 10 and 100 μg/mg stock solutions) with each of the test compounds was placed on the surface of the agar. Zones of inhibition were measured after incubating the plates at 30° C. for 24–48 hours.

The compounds were then screened against three strains of three species of microorganisms: *Candida albicans*, *Cryptococcus neoformans*, and *Aspergillus fumigatus* using a conventional double dilution technique. All tests reported in Table II were done by broth microdilution in yeast nitrogen base-glucose using an inoculum of $1 \times 10^4$ blastospores per ml; the cultures were incubated at 37° C. for 24 hours, and the minimum concentration (in μg/ml) that prevents visible growth was recorded as the minimum inhibitory concentration. The results are reported in Table II.

TABLE II

| | compound | | | |
|---|---|---|---|---|
| organism (strain) | Amphotericin B | Example I | Example II | Example III |
| C. albicans (1) | 1.6 | 1.6 | 6.4 | 6.4 |
| C. albicans (2) | 1.6 | 1.6 | 3.2 | 6.4 |
| C. albicans (3) | 1.6 | 1.6 | 3.2 | 6.4 |
| C. neoformans (1) | 0.8 | 1.6 | 3.2 | 0.8 |
| C. neoformans (2) | 0.8 | 3.2 | 3.2 | 0.8 |
| C. neofornams (3) | 0.8 | 0.8 | 3.2 | 0.8 |
| A. fumigatus (1) | 0.8 | 3.2 | 6.4 | >12.8 |
| A. fumigatus (2) | 1.6 | 3.2 | 3.2 | >12.8 |
| A. fumigatus (3) | 0.8 | 1.6 | 3.2 | 6.4 |

In addition to the in vitro data collected for the series of compounds according to the present invention, in vivo testing was also done as described in the following Examples V and VI.

EXAMPLE V

Ten immunocompetent ICR mice weighing 30 g each in three groups were inoculated intravenously with $3.2 \times 10^6$ colony forming units of *Candida albicans* (isolate NIH A) per mouse. MIC's (in DMSO and water at 24 and 48 hours were 3.03 mcg/ml; MIC's in water only at 24 and 48 hours were ≦6.06 mcg/ml. Twenty-four hours post inoculation and for ten succeeding days, each mouse in two of the groups was dosed (intraperitoneally) once per day with Amphotericin B (1 mg/kg of body weight) prepared in 5% dextrose, or the compound of Example II (30 mg/kg of body weight) prepared in sterile distilled water. The control animals were infected with *C. albicans*, but did not receive any treatment. The daily percent survival daily for each group is reported in Table III.

TABLE III

| Days (post-infection) | Control | Example II | Amphotericin B |
|---|---|---|---|
| 2 | 80% | 100% | 100% |
| 3 | 70% | 100% | 100% |
| 4 | 60% | 100% | 100% |
| 5 | 30% | 100% | 100% |
| 6 | 10% | 100% | 100% |
| 7 | 0% | 90% | 90% |
| 30 | | 90% | 90% |

EXAMPLE VI

Ten immunocompetent ICR mice weighing 30 g each in two groups were inoculated intravenously with 255 colony forming units of *Cryptococcus neoformans* (isolate NIH C-1) per mouse. MIC's (in DMSO and water at 48 and 72 hours were ≦6.06 mcg/ml; MIC's in water only at 48 hours was 1.51 mcg/ml, and at 72 hours was 3.03 mcg/ml. Twenty-four hours post inoculation and for ten succeeding days, each mouse in the test group was dosed (intraperitoneally) once per day the compound of Example II (30 mg/kg of body weight) prepared in sterile distilled Water. The control animals were infected with *C. neoformans*, but did not receive any treatment. The daily percent survival daily for each group is reported in Table III.

TABLE III

| Days (post-infection) | Control | Example II |
|---|---|---|
| 9 | 100% | 100% |
| 10 | 90% | 100% |
| 13 | 90% | 100% |
| 14 | 90% | 90% |
| 15 | 90% | 90% |

TABLE III-continued

| Days (post-infection) | Control | Example II |
|---|---|---|
| 16 | 70% | 90% |
| 17 | 70% | 90% |
| 18 | 60% | 90% |
| 19 | 60% | 90% |
| 20 | 40% | 90% |
| 21 | 30% | 90% |
| 22 | 30% | 70% |
| 25 | 30% | 70% |
| 26 | 20% | 60% |
| 27 | 10% | 60% |
| 28 | 0% | 50% |
| 29 | | 50% |
| 30 | | 40% |

A second in vivo assay was conducted as in Example VI with the exception that infection was with 488 colony forming units of *C. neoformans*, and that the test compound was administered 5 mg/kg, subcutaneous, BID. The daily percent survival daily for each group is reported in Table IV.

TABLE IV

| Days (post-infection) | Control | Example II |
|---|---|---|
| 11 | 100% | 100% |
| 12 | 90% | 80% |
| 13 | 80% | 60% |
| 14 | 70% | 60% |
| 15 | 70% | 60% |
| 16 | 60% | 60% |
| 17 | 40% | 60% |
| 19 | 40% | 60% |
| 20 | 30% | 60% |
| 21 | 30% | 60% |
| 22 | 20% | 60% |
| 23 | 20% | 40% |
| 24 | 20% | 20% |
| 27 | 20% | 20% |
| 28 | 20% | 10% |
| 29 | 20% | 10% |
| 30 | 20% | 0% |

The data in Tables III, IV and V clearly demonstrate the in vivo efficacy of the series of compounds according to the present invention.

The compounds according to the present invention, specifically those compounds of the general formula

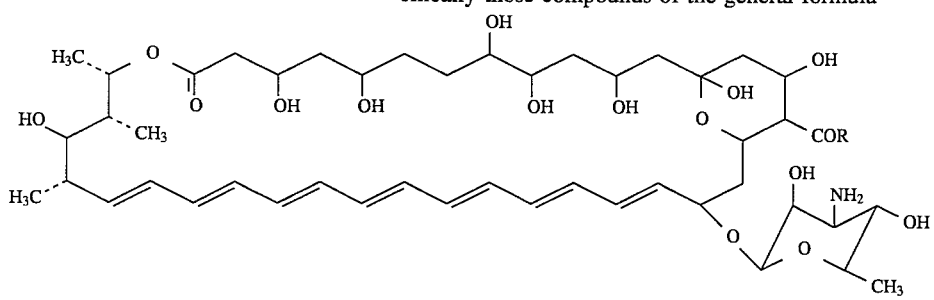

wherein R is $NH(CH_2CH_2O)_nR_1$, wherein n is an integer from 1 to 50; wherein $R_1$ is —H, $NH_2$, or a lower alkyl of $C_{1-6}$, and the pharmaceutical salts of these compounds may be used in the treatment of fungal diseases in mammals, particularly in man, in much the same manner as their amphiphilic parent compounds. They exhibit, because of their unique structures, improved pharmacological properties over conventional Amphotericin B.

With regard to the pharmaceutical salts of these compounds, it is readily apparent that the compounds of the present invention are basic, and as such they will readily form salts with acids. Thus, the compounds according to the present invention will react with both mineral and organic acids to form the corresponding acid salt. For example, these compounds may be reacted with mineral acids (such as hydrochloric, sulfuric or phosphoric acids) to form the corresponding hydrochoride, sulfate or phosphate salt; or these compounds may be reacted with organic acids (such as acetic, citric or tartaric acids) to form the corresponding salts. The formation of specific salts of these compound types is well known and documented in, for example, U.S. Pat. No. 2,908,611.

The compounds according to the present invention, are useful in the treatment of disease states in mammals when administered to the mammal in need of therapy in amounts of from about 5 mg to about 100 mg per kg of body weight per day. A preferred dose range would be from about 10 to about 30 per kg of body weight. Of course, this dosage regimen may be adapted to provide the optimum therapeutic response. for example, several divided doses may be administered daily, or the dose may be proportionally increased or reduced as indicated by the exigencies of the individual therapeutic situation. The compound may be administered as the free antibiotic or as an active agent in a pharmaceutical formulation that includes such carriers, fillers, extenders, dispersants, creams, gels and solutions as is common in the pharmaceutical formulatory arts. The compounds according to the present invention may be formulated for all modes of application including, for example, modes that encompass topical, intravenous, oral, intraperitoneally, subcutaneous, or intramuscular routes of administration.

Thus while I have illustrated and described the preferred embodiment of my invention, it is to be understood that this invention is capable of variation and modification, and I therefore do not wish to be limited to the precise terms set forth, but desire to avail myself of such changes and alterations which may be made for adapting the invention to various usages and conditions. Such variations and modifications, for example, would include the modification of other amphiphilic antibiotics, such as the antibiotic Nystatin which has a very similar structure to Amphotericin B, by a "R" group as defined above (Nystatin and Amphotericin B have been shown to act by similar mechanisms in sterol containing planar bilayer systems, and while somewhat lower in potency against fungal organisms as compared with Amphotericin B, it may be far less toxic toward mammalian cells and is used generally against topical, oral and vaginal infections in man). Thus, such variations and modifications are properly intended to be within the full range of equivalents, and therefore within the purview of the following claims.

Having thus described my invention and the manner and a process of making and using it in such full, clear, concise and exact terms so as to enable any person skilled in the art to which it pertains, or with which it is most nearly connected, to make and use the same;

I claim:

1. An amphiphilic compound of the formula:

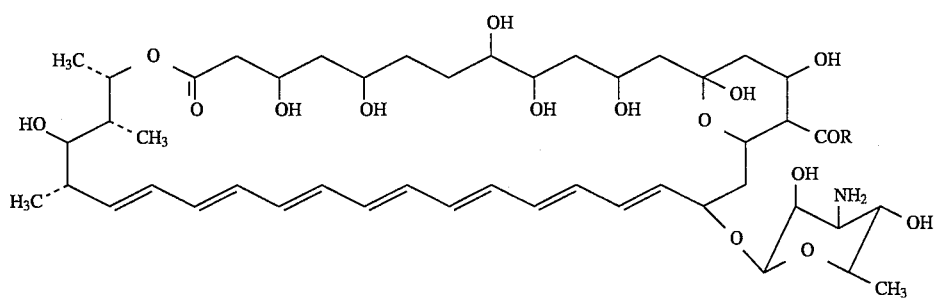

wherein R is $NH(CH_2CH_2O)_nR_1$, wherein n is an integer from 1 to 50; and wherein $R_1$ is hydrogen, $-NH2$, or a lower alkyl of $C_{1-6}$, or a pharmaceutical salt thereof.

2. An amphiphilic compound of the formula:

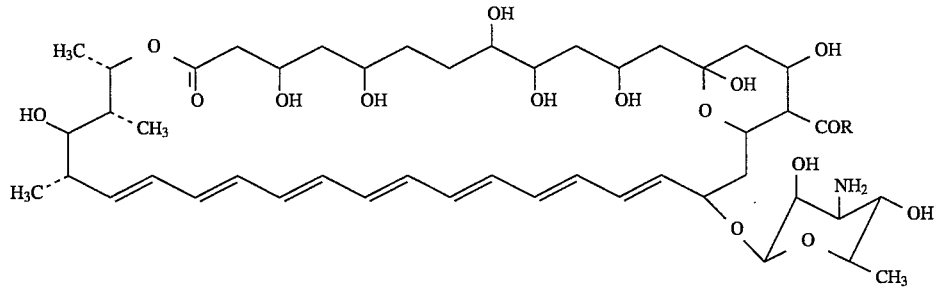

wherein R is $NH(CH_2CH_2O)_nR_1$, wherein n is an integer from 1 to 50; and wherein $R_1$ is hydrogen or a lower alkyl of $C_{1-6}$, or a pharmaceutical salt thereof.

3. An amphiphilic compound according to claim 1 wherein $R_1$ is hydrogen, or a lower alkyl of $C_{1-6}$.

4. An amphiphilic compound according to claim 2 wherein n is from 1 to about 20.

5. An amphiphilic compound according to claim 4 wherein n is from 1 to about 17.

6. An amphiphilic compound according to claim 5 wherein n is from about 3 to about 15.

7. An amphiphilic compound according to claim 2 wherein $R_1$ is a lower alkyl of from 1 to 6 carbon atoms.

8. An amphiphilic compound according to claim 7 wherein $R_1$ is a lower alkyl of from 1 to 3 carbon atoms.

9. An amphiphilic compound according to claim 8 wherein $R_1$ is methyl.

10. An amphiphilic compound according to claim 2 wherein n is 3 to 15, and $R_1$ is methyl.

11. The compound according to claim 10 wherein n is 3.

12. The compound according to claim 10 wherein n is 6.

13. The compound according to claim 10 wherein n is 15.

14. A method for improving the antibiotic property of an analogue of Amphotericin B having a —COOH moiety, said analogue having a first critical micelle concentration and that functions by disrupting the cellular membrane of the organism to which it is targeted, said improvement being achieved by altering the chemical structure of said analogue by the substitution of an oligo(ethylene glycol) conjugate in lieu of the OH portion of said —COOH moiety, thereby raising the critical micelle concentration from said first to a second critical micelle concentration.

* * * * *